United States Patent
Flohr et al.

(10) Patent No.: US 10,420,522 B2
(45) Date of Patent: Sep. 24, 2019

(54) GENERATING CONTRAST-ENHANCED IMAGE DATA BASED ON MULTI-ENERGY X-RAY IMAGING

(71) Applicant: Siemens Healthcare GmbH, Erlangen (DE)

(72) Inventors: Thomas Flohr, Uehlfeld (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 226 days.

(21) Appl. No.: 15/428,729

(22) Filed: Feb. 9, 2017

(65) Prior Publication Data

US 2017/0245816 A1    Aug. 31, 2017

(30) Foreign Application Priority Data

Feb. 29, 2016 (DE) .................... 10 2016 203 257

(51) Int. Cl.
*A61B 6/00* (2006.01)
*A61B 6/03* (2006.01)

(52) U.S. Cl.
CPC .............. *A61B 6/481* (2013.01); *A61B 6/032* (2013.01); *A61B 6/405* (2013.01); *A61B 6/4007* (2013.01);
(Continued)

(58) Field of Classification Search
None
See application file for complete search history.

(56) References Cited

U.S. PATENT DOCUMENTS

| 2013/0083989 A1 | 4/2013 | Flohr et al. |
| 2015/0272522 A1* | 10/2015 | Robinson ............. A61B 6/4035 378/5 |
| 2015/0348292 A1* | 12/2015 | Taguchi ................ G06T 11/005 382/131 |

FOREIGN PATENT DOCUMENTS

DE        102011083727 A1    4/2013

OTHER PUBLICATIONS

Primak. A. N. et al: "Improved dual-energy material discrimination for dual-source CT by means of additional spectral filtration"; In: Medical Physics 36 (4 ); pp. 1359-1369; 2009.
(Continued)

*Primary Examiner* — Hoon K Song
(74) *Attorney, Agent, or Firm* — Harness, Dickey & Pierce, P.L.C.

(57) ABSTRACT

An X-ray imaging method is for generating contrast-enhanced image data relating to an examination region of an object to be examined. In an embodiment of the method, first contrast-agent influenced measured X-ray projection data with a first X-ray energy spectrum and at least one set of second contrast-agent influenced measured X-ray projection data with a second X-ray energy spectrum are acquired from the examination region. Subsequently, image data assigned to a third X-ray energy spectrum with a third mean energy, based on the first and at least second measured X-ray projection data is reconstructed based on the first and at least second measured X-ray projection data that has been acquired. A mean energy of the first X-ray energy spectrum and a mean energy of the second X-ray energy spectrum are selected as a function of a dimension parameter value of the object that is to be examined.

21 Claims, 3 Drawing Sheets

(52) U.S. Cl.
CPC .......... *A61B 6/4014* (2013.01); *A61B 6/4241* (2013.01); *A61B 6/482* (2013.01); *A61B 6/5205* (2013.01); *A61B 6/504* (2013.01); *A61B 6/507* (2013.01)

(56) References Cited

OTHER PUBLICATIONS

Leng Shuai et al: "Maximizing Iodine Contrast-to-Noise Ratios in Abdominal CT Imaging througti Use of Energy Domain Noise Reduction and Virtual Monoenergetic Dual-Energy CT(1)", In: Radiology 276 (2); pp. 562-570.; 2015.
Yu Lifeng et al: "Dual-Energy CT-Based Monochromatic Imaging"; American Journal of Roentenology Nov. 2012; 199. Jg.; pp. 9-15; 2012.
Alvarez, Robert E. et al.: Energy-selective Reconstructions in X-ray Computerized Tomography, Phys. Med. Biol., 1976, vol. 21, No. 5, pp. 733-744.
Grant, K.L., et.al.: "Assessment of an Advanced Image-Based Technique to Calculate Virtual Monoenergetic Computed Tomographic Images From a Dual-Energy Examination to Improve Contrast-to-Noise Ratio in Examinations Using Iodinated Contrast Media", in: Investigative Radiology; 2014.
Yu Lifeng et al: "Optimal Tube Potential for Radiation Dose Reduction in Pediatric CT: Principles, Clinical Implementations, and Pitfalls"; In: Radiographics 31/ May-Jun. 2011; pp. 835-848; 2011.
McCollough C. H. et al: "Dual- and Multi-Energy CT: Principles, Technical Approaches, and Clinical Applications"; In: Radiology 276 (3) 20155; pp. 637-653; Sep. 2015; 2015.
German Office Action for German Patent Application No. 10 2016 203 257.7 dated Nov. 17, 2016.

\* cited by examiner

FIG 3

GENERATING CONTRAST-ENHANCED IMAGE DATA BASED ON MULTI-ENERGY X-RAY IMAGING

PRIORITY STATEMENT

The present application hereby claims priority under 35 U.S.C. § 119 to German patent application number DE 102016203257.7 filed Feb. 29, 2016, the entire contents of which are hereby incorporated herein by reference.

FIELD

At least one embodiment of the invention generally relates to an X-ray imaging method for generating contrast-enhanced image data. At least one embodiment of the invention further generally relates to an image data generating device. In addition, at least one embodiment of the invention generally relates to a computer tomography system.

BACKGROUND

With the aid of modern imaging methods, two- or three-dimensional image data, which can be used for visualizing an examination object that has been imaged and in addition to this can be used for further applications, are frequently generated.

The imaging methods are frequently based on the detection of X-ray radiation, with "measured projection data" being generated. For example, measured projection data can be acquired with the aid of a computer tomography system (CT system). In CT systems, a combination of X-ray source and X-ray detector that is disposed opposite the source and arranged on a gantry generally rotates round a measurement space, in which the examination object (mostly referred to hereinafter without restricting the generality as the patient). The center of rotation (also known as the "isocenter") coincides with what is known as a system axis z. In one or a plurality of circuits, the patient is radiated with X-ray radiation from the X-ray source, with measured projection data or measured X-ray projection data being acquired with the aid of the facing X-ray detector.

The measured projection data that is generated is dependent in particular on the design of the X-ray detector. X-ray detectors usually comprise a plurality of detection units that are generally arranged in the form of a regular pixel array. The detection units each generate a detection signal for the X-ray radiation that impinges on the detection units, which signal is analyzed at specific points in time with respect to intensity and spectral distribution of the X-ray radiation in order to draw conclusions relating to the examination subject and measured projection data.

With the aid of CT imaging, for a long time it was "only" static anatomical structures that could be reproduced in image form. On the other hand, dynamic imaging and functional imaging using computer tomography were not possible for a long time, also among other things because of too high a level of radiation exposure for the patient. In the last few years, however, technological progress has meant that the possibilities for dynamic imaging have improved and have found their way into clinical routine.

What are known as dynamic CT imaging methods include images of measured CT projection data for the same examination region over a longer period of, for example, 5 to 50 s and the subsequent time-resolved reconstruction of CT image data at various times in the aforementioned time period. Essentially, two applications are common here: a first application relates to the representation of the influx and efflux of contrast agent into a vascular system. This type of dynamic imaging is also known as CT angiography. A special case of this is the "neuro DSA technique", in which the image structures that correspond with bones can be removed from a contrast agent image and a native image by registering one on top of the other. A second application relates to representing the development over time of the contrast agent enrichment in an organ. This application is also known as dynamic CT perfusion imaging. It shows, for example, perfusion defects in the brain tissue following a stroke, makes circulatory disorders in the myocardium visible, or characterizes tumors, for example in the lung or in the abdomen, by their contrast agent enrichment and possibly follows up their response to treatment.

In order to improve the image contrast of the contrast agent used, iodine, for example, and to reduce the radiation dose for the patient, lower voltages in the X-ray tube are generally set, for dynamic CT scans, at between 70 kV and 100 kV, for instance. When such low tube voltages are selected, the mean energy level in the X-ray energy spectrum generated by an X-ray tube moves down to lower values. For example, at an X-ray tube voltage of 80 kV, the mean energy in the X-ray spectrum is around 55 keV. The X-ray energy spectrum shall be understood as the energy distribution of the X-ray quanta generated by an X-ray tube.

When reference is made hereinafter to energy in the X-ray spectrum or in the X-ray energy spectrum, this usually refers to the mean energy of the X-ray energy spectrum for the X-ray radiation that has been emitted. In the case of monoenergetic X-ray images, this mean energy can also be identical to a single energy, which corresponds in this specific case to the energy of the X-ray quanta from which the respective monoenergetic X-ray image can be reconstructed. At such low energies, we are closely approaching the K-edge of the contrast agent iodine, which occurs at an energy of 33 keV. As a result thereof, in the CT image iodine appears with higher CT values because it absorbs higher percentages of the X-ray radiation. In this way, a higher level of image noise can be allowed for a desired contrast-noise ratio and thus the radiation dose for the patient can be reduced.

It is precisely in dynamic CT imaging that a low radiation dose is required due to the long image acquisition time. However, in conventional CT systems, at low tube voltages, in particular at 80 kV, the available power for the X-ray radiation source is limited, such that, in particular in dynamic CT examinations in the trunk area of a patient, the tube current that is required for the desired contrast-noise ratio is only achieved in thinner patients and therefore only thinner patients can be examined using a low tube voltage. For stout patients on the other hand, the capacity of the X-ray sources is no longer adequate, such that increased image noise and other artifacts, such as streaks or an instability of CT values for example, appear in the CT images, which far outweigh the positive effect of the low tube voltages on the contrast/noise ratio.

If the power available to the X-ray source in the desired low tube voltages (80 kV) is not adequate with conventional dynamic CT imaging methods, then the examinations are carried out at higher tube voltages (100 kV), at which an increased power is available to the X-ray sources. However, at 100 kV the iodine contrast in the image is lower. In order to adhere to a specific contrast/noise ratio, the image noise therefore has to be suppressed more than at lower tube voltages and the radiation dose therefore has to be increased.

For example, when using a tube voltage of 100 kV, a 30% higher radiation dose is required than at a tube voltage of 80 kV. Since specific dose limits have to be adhered to, the range of applications for the aforementioned imaging methods is reduced considerably.

SUMMARY

The inventors have recognized that a problem therefore arises of providing a contrast-enhanced X-ray imaging method and a corresponding image data generating device that allow a good image quality with low radiation exposure.

In at least one embodiment of the present application, this problem is solved by an X-ray imaging method for generating contrast-enhanced image data, an image data generating device and/or a computer tomography system.

In the X-ray imaging method according to at least one embodiment of the invention, preferably a CT-X-ray imaging method, for generating contrast-enhanced image data relating to an examination region of an object that is to be examined, of a patient, for example, one set of first contrast-agent enhanced measured X-ray projection data with a first X-ray energy spectrum and at least one set of second contrast-agent enhanced measured X-ray projection data with a second X-ray energy spectrum relating to the examination region is acquired.

The image data generating device according to at least one embodiment of the invention comprises an X-ray energy determination unit for determining a mean energy for determining a first energy of a first X-ray energy spectrum and a mean energy of a second X-ray energy spectrum as a function of the dimensions parameter value for an object that is to be examined. For example, the X-ray energy determination unit can obtain information on the dimensions of an object to be examined via an input interface. This information is evaluated by the X-ray energy determination unit for example, using known theoretical relationships between the dimensions of the subject to be examined and the absorption properties thereof in order to determine the degree to which X-ray radiation is absorbed by the subject that is to be examined in the region that is to be examined. As a function thereof, the selection of the mean energy of the first X-ray energy spectrum and of the second X-ray energy spectrum then ensues. Here, the size of the values of the mean energies for the two X-ray energy spectra is selected such that image noise in image data generated with the aid of the first and second X-ray energy spectra does not exceed a maximum value. Alternatively, it is also possible, for a case where the image noise is acceptable at all energies, for the X-ray dose required for the acquisition of the measured projection data to be reduced by selecting suitable mean energy values in both the X-ray energy spectra.

The computer tomography system according to at least one embodiment of the invention comprises an image data generating device according to at least one embodiment of the invention. The image data generating device according to at least one embodiment of the invention can form in particular part of a control device in the computer tomography system.

The key components of the image data generating device according to at least one embodiment of the invention can for the most part be designed in the form of software components. This relates in particular to the X-ray energy determination unit, the control unit, the measured projection data acquisition unit and the image data reconstruction unit. In principle, however, some of these components can also be implemented in the form of software-supported hardware, for example, FPGAs or suchlike, in particular when it is a matter of making quick calculations. Likewise, the interfaces can be designed as software interfaces, for example, if it is only a matter of importing data from other software components. However, they can also be designed as hardware-based interfaces that are activated by appropriate software.

A mainly software-based design has the advantage that image data generating devices or a control device of computer tomography systems that have already been used hitherto can be upgraded in a simple manner by way of a software update so that they can work in the manner according to at least one embodiment of the invention. In this respect, the problem is solved by a corresponding computer program product with a computer program that can be loaded directly into a memory unit of an image data generating device according to at least one embodiment of the invention or of a memory unit of a control device of a computer tomography system and includes program segments in order to carry out all the steps in the method according to at least one embodiment of the invention when the computer program is run in the image data generating device or the control device of the computer tomography system.

Such a computer program product can optionally include additional components alongside the computer program, such as for example, documentation and/or additional components, including hardware components, such as for example, hardware keys (dongles etc.) for using the software.

For transport to the memory unit of the image data generating device and/or for storage on the image data generating device, a computer-readable medium, for example, a memory stick, a hard drive or another transportable or fixedly incorporated data-carrier can be used, on which the transferable and executable program segments of the computer program are stored by a computation unit of the image data generating device. The computation unit can include, for example, one or a plurality of microprocessors or suchlike working in combination.

BRIEF DESCRIPTION OF THE DRAWINGS

The invention is described again hereinafter in further detail with reference to the attached figures by way of example embodiments. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the X-ray imaging method according to at least one embodiment of the invention, preferably a CT-X-ray imaging method, for generating contrast-enhanced image data relating to an examination region of an object that is to be examined, of a patient, for example, one set of first contrast-agent enhanced measured X-ray projection data with a first X-ray energy spectrum and at least one set of second contrast-agent enhanced measured X-ray projection data with a second X-ray energy spectrum relating to the examination region is acquired.

To acquire the measured X-ray projection data, a "dual-energy" measurement method can be used for example, in which X-ray radiation is emitted with different X-ray energy spectra in the direction of a region that is to be examined, is partially absorbed by the region and the transmitted portion of the X-ray radiation can subsequently be detected by different detectors.

The detectors do not have to be spectral. In the case of dual source, a method in which two separate X-ray sources with different tube energies are used or in that of kV-switching, in which the electric voltage in the X-ray source is switched between different values, conventional detectors are used even today. Here the data acquisition ensues using different spectra. Alternatively, the spectral data can also be acquired with a spectrally resolving detector. Here the data acquisition with only one spectrum is sufficient. The energy separation is achieved in this case on the detector (unlike the methods above, in which different spectra are used). Generally it is also possible to combine the above methods with a spectral detector.

On the basis of the first and at least second measured X-ray projection data that has been acquired, pseudo-monoenergetic image data is preferably obtained, which data is assigned to a third X-ray energy spectrum with a third mean energy. Here a mean energy of the first X-ray energy spectrum and a mean energy of the second X-ray energy spectrum are selected as a function of a dimension parameter value of the subject to be examined. The values for the mean energy in the first X-ray energy spectrum and the second X-ray energy spectrum preferably differ from one another.

The third X-ray energy spectrum preferably has a single X-ray energy. That is, a monoenergetic X-ray energy spectrum is preferably provided as a third X-ray energy spectrum, the third "mean" energy then representing the individual energy of the monoenergetic X-ray energy spectrum. When reference is made hereinafter to a third X-ray energy spectrum with a third mean energy, this shall, particularly preferably, likewise always include the specific embodiment in which pseudo-monoenergetic X-ray images are generated on the basis of an individual energy, and the "mean" energy then corresponds to this individual energy value.

Therefore, based on the multispectral measured X-ray projection data that has been acquired, an X-ray image with an X-ray spectrum or a third mean energy, preferably an individual energy value is calculated as a kind of mixed image, also known in the event of the individual energy value as a pseudo-monoenergetic mixed image. Advantageously, the third mean energy or the individual third energy value is selected such that the image contrast/noise ratio of the imaging, which ratio has been influenced by a previously added contrast agent, is particularly favorable in the case of this third energy. However, the image noise is often very pronounced even in the case of energies, at which the contrast agent is particularly effective.

Now this drawback is overcome according to at least one embodiment of the invention by the first and the second measured projection data being acquired at a different energy than the third energy and in fact as a function of the dimensions or the absorption of the object that is to be examined. Thin people, for example, have a clearly lower absorption than fatter people.

In order to compensate for the increasing image noise that occurs with a greater absorption of the X-ray radiation, according to at least one embodiment of the invention, the electric voltage of the X-ray tubes, there usually being two X-ray tubes in the case of dual energy imaging, or the mean energy of the X-ray radiation used for the acquisition of the first and second measured projection data is raised. At higher electric voltages, X-ray tubes have the characteristic that they have an increased radiation output as the available tube currents are higher than at low voltages. With an increased output of the X-ray tubes, the image noise is reduced due to the increased percentage of transmitted X-ray radiation.

According to at least one embodiment of the invention, therefore, the advantages of imaging using an X-ray energy spectrum with an increased mean energy are combined with the advantages of a in this case virtual imaging at a lower mean energy or preferably at an individual energy value at which the image contrast is particularly strong, such that when generating the virtual image data, an improved image contrast/noise ratio is achieved.

Alternatively, where the image contrast/noise ratio is unchanged, the required X-ray dose can also be reduced. This may be the case, for example, in the examination of thin patients, in the case of whom images could basically be acquired using X-ray radiation with a mean energy, and in the case of whom the image contrast/noise ratio is still sufficient, even though a higher radiation dose would traditionally be required than in the method according to at least one embodiment of the invention.

The image data generating device according to at least one embodiment of the invention comprises an X-ray energy determination unit for determining a mean energy for determining a first energy of a first X-ray energy spectrum and a mean energy of a second X-ray energy spectrum as a function of the dimensions parameter value for an object that is to be examined. For example, the X-ray energy determination unit can obtain information on the dimensions of an object to be examined via an input interface. This information is evaluated by the X-ray energy determination unit for example, using known theoretical relationships between the dimensions of the subject to be examined and the absorption properties thereof in order to determine the degree to which X-ray radiation is absorbed by the subject that is to be examined in the region that is to be examined. As a function thereof, the selection of the mean energy of the first X-ray energy spectrum and of the second X-ray energy spectrum then ensues. Here, the size of the values of the mean energies for the two X-ray energy spectra is selected such that image noise in image data generated with the aid of the first and second X-ray energy spectra does not exceed a maximum value. Alternatively, it is also possible, for a case where the image noise is acceptable at all energies, for the X-ray dose required for the acquisition of the measured projection data to be reduced by selecting suitable mean energy values in both the X-ray energy spectra.

An additional part of the image data generating device according to at least one embodiment of the invention is a control unit to activate one or a plurality of X-ray sources in a CT system, such that X-ray radiation is generated in each case using the first X-ray energy spectrum and the second X-ray energy spectrum, in each case with the first and second mean energy that has been determined. The image data generating device according to the invention additionally includes a measured projection data acquisition unit for acquiring first contrast-agent enhanced measured X-ray projection data using the first X-ray energy spectrum and second contrast-enhanced measured X-ray projection data using the second X-ray energy spectrum of an examination region in an examination object. Moreover, the image data generating device according to at least one embodiment of the invention comprises an image data reconstruction unit for reconstructing pseudo-monoenergetic image data that is assigned to a third X-ray energy spectrum, preferably to an individual third X-ray energy value, on the basis of the first and at least second measured X-ray projection data.

A method for reconstructing or calculating pseudo-monoenergetic image data is known from Alvarez R. E. and Macovski A. "Energy-selective reconstructions in x-ray computed tomography", Phys. Med. Biol. 21, 733-744 (1976), the entire contents of which are hereby incorporated herein by reference.

A particularly suitable method for reconstructing or calculating pseudo-monoenergetic image data is described in K. L. Grant et al. "Assessment of an Advanced Image-Based Technique to Calculate Virtual Monoenergetic Computed Tomographic Images From a Dual-Energy Examination to Improve Contrast-To-Noise Ratio in Examinations Using Iodinated Contrast Media", Investigative Radiology 2014; 00: 00-00), the entire contents of which are hereby incorporated herein by reference.

In the generation of pseudo-monoenergetic image data, there ensues a breakdown of the measured projection data in the raw data space or of the image data in the image data space constructed therefrom. For example, when an iodine contrast agent is used, the data is broken down into an iodine/lime component and into a water/soft tissue component and then an attenuation value (HU value) is calculated for the respective voxel with the aid of tabulated values for an X-ray energy value (keV-value) selected by the user, based on density values.

The computer tomography system according to at least one embodiment of the invention comprises an image data generating device according to at least one embodiment of the invention. The image data generating device according to at least one embodiment of the invention can form in particular part of a control device in the computer tomography system.

The key components of the image data generating device according to at least one embodiment of the invention can for the most part be designed in the form of software components. This relates in particular to the X-ray energy determination unit, the control unit, the measured projection data acquisition unit and the image data reconstruction unit. In principle, however, some of these components can also be implemented in the form of software-supported hardware, for example, FPGAs or suchlike, in particular when it is a matter of making quick calculations. Likewise, the interfaces can be designed as software interfaces, for example, if it is only a matter of importing data from other software components. However, they can also be designed as hardware-based interfaces that are activated by appropriate software.

A mainly software-based design has the advantage that image data generating devices or a control device of computer tomography systems that have already been used hitherto can be upgraded in a simple manner by way of a software update so that they can work in the manner according to at least one embodiment of the invention. In this respect, the problem is solved by a corresponding computer program product with a computer program that can be loaded directly into a memory unit of an image data generating device according to at least one embodiment of the invention or of a memory unit of a control device of a computer tomography system and includes program segments in order to carry out all the steps in the method according to at least one embodiment of the invention when the computer program is run in the image data generating device or the control device of the computer tomography system.

Such a computer program product can optionally include additional components alongside the computer program, such as for example, documentation and/or additional components, including hardware components, such as for example, hardware keys (dongles etc.) for using the software.

For transport to the memory unit of the image data generating device and/or for storage on the image data generating device, a computer-readable medium, for example, a memory stick, a hard drive or another transportable or fixedly incorporated data-carrier can be used, on which the transferable and executable program segments of the computer program are stored by a computation unit of the image data generating device. The computation unit can include, for example, one or a plurality of microprocessors or suchlike working in combination.

The claims and also the description that follows each define particularly advantageous embodiments and further developments of the present invention, it also being possible in particular for the claims in one claim category to be further developed by analogy with the dependent claims in a different claim category. In addition, it is possible in the context of the invention for the various features of different example embodiments and claims to be also used in combination for new example embodiments.

In one variant of the X-ray imaging method according to at least one embodiment of the invention, energy values selected as the mean energy for the first and the second X-ray energy spectrum are values at which a lower image noise occurs compared with the third mean energy. That is, in X-ray image acquisition according to at least one embodiment of the invention, the level of interference unrelated to the image information itself is reduced by the fact that the energy spectra of the X-ray radiation with which the first and second measured projection data is acquired are moved to values at which the image noise is reduced.

A higher value can be preferably be selected as the mean energy for the first and the second X-ray energy spectrum than for a mean energy of the third X-ray energy spectrum. At higher energies of the X-ray radiation applied, the percentage of absorbed X-ray radiation decreases relative to the total X-ray radiation applied. This consequently results in an improved signal/noise ratio at higher energies, as a result of which the image quality is improved.

Examples of suitable X-ray tube voltages are 120 keV and 140 keV. The use of such high tube voltages has the advantage that the high power reserves of the X-ray tube unit that are available at high voltages can be used as standard, such that in particular dynamic CT examinations are possible without a specific low kV protocol and yet are possible at a reduced radiation dose.

In a preferred embodiment of the X-ray imaging method according to at least one embodiment of the invention, the X-ray imaging method includes a dynamic time-resolved imaging method, preferably a CT-angiography method or a CT perfusion imaging method. In particular with dynamic imaging methods, the period of time for which a specific region in a specific state of a specific procedure can be irradiated is very restricted. However, this means, in particular at low X-ray energies, that the X-ray dose that can be applied in each case in a corresponding time interval is likewise very restricted. In order to reduce the resulting increased image noise, the X-ray imaging method according to at least one embodiment of the invention can be used in a particularly effective manner, since the image noise is thus reduced.

In the imaging method according to at least one embodiment of the invention, an X-ray energy distribution around a mean X-ray energy is preferred as a third X-ray energy spectrum, at which there is an increased contrast in the image data that is to be generated. In this way, the advantages of image acquisition at high energies, that is a reduced image noise, and energies in regions in which a particularly highly pronounced image contrast is expected can be combined, such that a particularly favorable contrast/noise ratio is advantageously achieved in the image acquisition.

In a particularly effective variant of the X-ray imaging method according to at least one embodiment of the invention, a distribution around a third mean energy is used as a third X-ray energy spectrum, which third mean energy is near to an X-ray absorption edge of a contrast agent used for contrast enhancement. When X-ray radiation is applied with a mean energy near to the X-ray absorption edge of a contrast agent that is used, a greater part of the radiation is absorbed in regions in which the contrast agent is present, so these regions therefore appear brighter than when X-ray radiation is applied with a higher energy. Consequently, in this variant of the X-ray imaging method according to at least one embodiment of the invention, an improved contrast/noise ratio is achieved.

In the X-ray imaging method according to at least one embodiment of the invention, iodine is particularly preferably used as a contrast agent. As a result thereof, a particularly favorable contrast/noise ratio is achieved if the third X-ray energy has an energy value of between 35 keV and 60 keV, preferably between 40 keV and 45 keV. This is related to the fact that the K-edge or K-absorption edge of iodine is at an energy of 33 keV, such that the aforementioned effect occurs, whereby a major part of the incident X-ray radiation is absorbed in the regions treated with iodine and these regions therefore appear very bright on the X-ray image.

In a variant of the X-ray imaging method according to at least one embodiment of the invention with particularly advantageous applications, the dimension parameter value contains data regarding the body mass and/or the dimensions of the body and/or the BMI of the object to be examined. This kind of data can be used to acquire an absorption profile of an examination object. The aforementioned data can be obtained, for example, by acquiring a topogram in advance. For imaging the outlines of an examination object, cameras or other types of image acquisition devices can be used. In addition, for image acquisition, reference data that makes it possible to establish a relationship between the dimensions of an examination object and the absorption caused thereby can also be used.

In the context of a preferred variant of the X-ray imaging method according to at least one embodiment of the invention, for the acquisition of the first and at least second measured X-ray projection data, a multi-source CT system, preferably a dual-source CT system, is used, the first and at least second measured X-ray projection data preferably being acquired simultaneously.

In such a multi-source CT system, there is a plurality of X-ray sources with a different X-ray spectrum, such that what is known as a multi-energy imaging method can be carried out.

In a particularly feasible variant of the X-ray imaging method according to at least one embodiment of the invention, a single-source CT system with a single X-ray tube is used for the acquisition of the first and at least second measured X-ray projection data. Here, the first and at least second measured X-ray projection data is acquired via a rapid switchover of an electric voltage on the X-ray tube.

This means that in this case the system does indeed have only one X-ray source, the X-ray tube voltage of which is switched over between two different voltage values, however, in order to generate X-ray radiation with different X-ray energy spectra for the first and second measured projection data.

In a specific variant of the X-ray imaging method according to at least one embodiment of the invention, a photon-counting X-ray detector is used for the acquisition of the first and at least second measured X-ray projection data. A photon-counting X-ray detector is particularly well suited to spectrally-resolved acquisition of measured projection data.

In a specific variant of the X-ray imaging method according to at least one embodiment of the invention, image data is additionally acquired for a fourth X-ray energy with a high energy value, based on the first and at least second measured X-ray projection data, wherein the additional image data corresponds to image data that is not contrast-enhanced. At high energies, pseudo-monoenergetic image data has the characteristic that the image noise is suppressed by contrast agents, such as iodine, for example. Consequently, an image that is not contrast-enhanced can virtually be generated in addition. Such an image can be helpful, for example, if the scanning for the perfusion imaging has been started too late and reference data, also known as baseline data, is still lacking. In this context, what is considered to be a high energy value is an energy that is high relative to the energy of the relevant absorption edge of the contrast agent used. A high energy value shall in particular be higher than the third (mean) energy used to generate the pseudo-monoenergetic image data.

In a particularly effective variant of the X-ray imaging method according to at least one embodiment of the invention, in the image reconstruction a filtering method is carried out to reduce the image noise. Such a filtering method is described in detail in DE 10 2011 083 727 A1, the entire contents of which are hereby incorporated herein by reference. In this way, the image noise can be reduced considerably in pseudo-monoenergetic image data. Consequently at low energies, for example when using conventional dual-energy CT systems such as SOMATOM Definition Flash, pseudo-monoenergetic images have a higher contrast-noise ratio than images that are acquired directly using mono-energy imaging techniques at energies in the region of the absorption edge of a contrast agent that is used.

Figure 1:
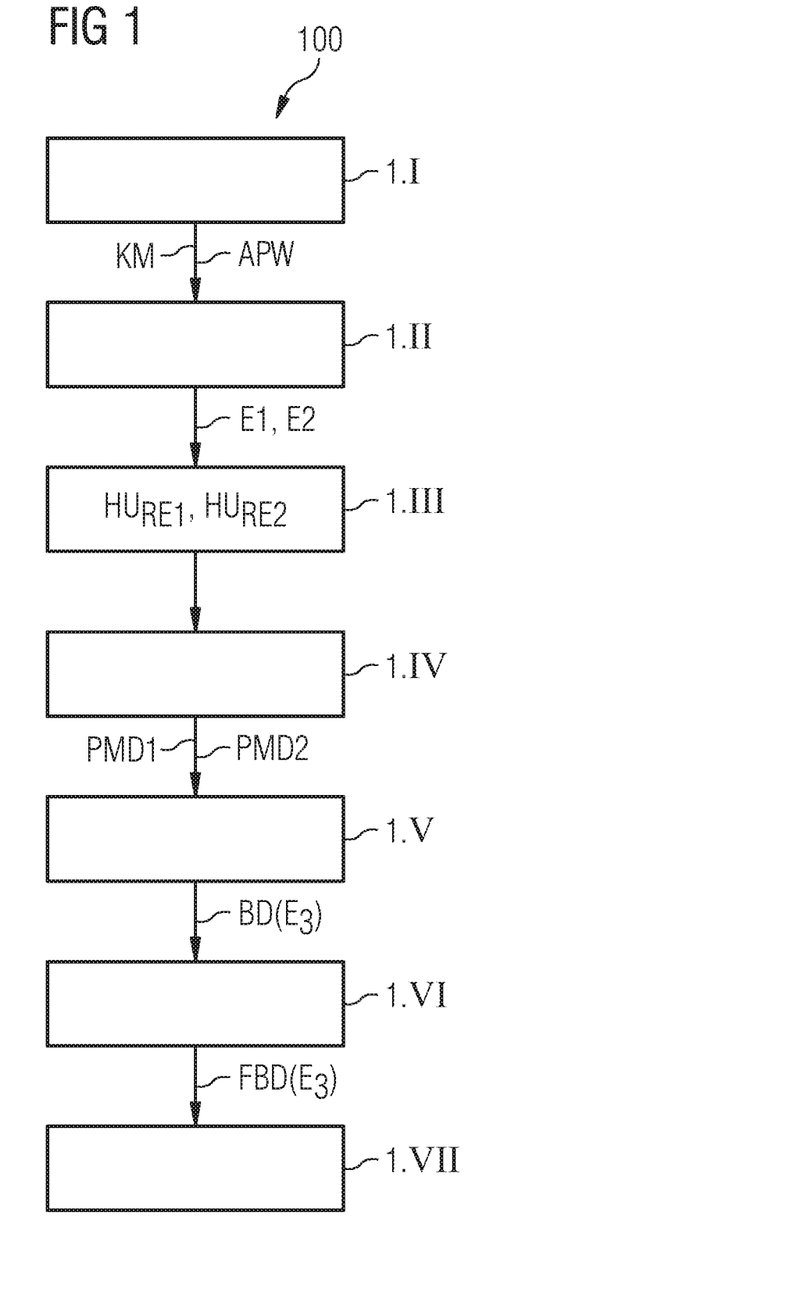
FIG. 1 shows a flow diagram that illustrates a method for generating contrast-enhanced image data of an examination region of an object to be examined.

FIG. 1 shows a flow diagram 100, which illustrates a dynamic CT imaging method with the aid of what is known as the dual-energy technique, in which contrast-enhanced image data is generated by a stout patient according to one example embodiment of the invention. In a dynamic imaging method with the aid of the dual-energy technique, there follows a dynamic, time-resolved acquisition of two measured projection data sets PMD1, PMD2, each of which are generated by X-ray radiation with different X-ray energy spectra RE1, RE2 using different mean energies E1, E2. To generate the X-ray radiation using different X-ray energy spectra RE1, RE2, it is possible, for example, to use two X-ray sources 15a, 15b (see FIG. 3), which emit X-ray radiation at different X-ray energies E1, E2 or X-ray energy spectra RE1, RE2.

In the context of the dynamic imaging method, in step 1.I first data relating to the dimensions of an object that is to be examined, a patient, for example, is acquired. This data, also referred to as dimension parameter values relating to the subject to be examined APW, can include for example, how fat the patient is, their size, their BMI, their body mass, a density distribution inside the patient's body or other data, with which the extent of the absorption of the X-ray radiation by the patient can be determined or estimated in the region that is being examined. Furthermore, information about the type of contrast agent (KM) administered before the start of the imaging method is acquired. Different contrast agents may include different X-ray absorption edges, also known for short as the X-ray edge. The position of the X-ray edge relative to the energy E3 in a pseudo-monoenergetic X-ray image that is to be acquired later impacts on the image contrast of this X-ray image, such that knowledge of the energy value of the X-ray absorption edge of the contrast agent (KM) determines the image quality of the X-ray image that is to be reconstructed with the aid of the imaging method according to the invention.

Subsequently, in step 1.II, based on the dimension parameter value (APW) data acquired in step 1.I, contrast agent (KM) values for first and second mean energies $E_1$, $E_2$ of different X-ray spectra $R_{E1}$, $R_{E2}$ of X-ray radiation is acquired, with which the region to be examined (FOV) of the patient O is to be examined later.

In step 1.III, X-ray radiation is generated by two different X-ray tubes with high-energy first and second X-ray energy spectra $R_{E1}$, $R_{E2}$. These X-ray energy spectra $R_{E1}$, $R_{E2}$ are generated with the aid of high first and second tube voltages $HU_{RE1}$, $HU_{RE2}$. With the aid of the first and second tube voltages $HU_{RE1}$ and $HU_{RE2}$, the X-ray tubes are excited so as to generate X-ray radiation using the first and second mean energies $E_1$, $E_2$ that have been determined. In particular when using iodine as a contrast agent, the first and second tube voltages $HU_{RE1}$, $HU_{RE2}$, for example, are preferably 120 kV and 140 kV.

In step 1.IV, the X-ray radiation generated by the two X-ray sources with different first and second X-ray spectra or X-ray energy spectra at high mean energies $E_1$, $E_2$ by two X-ray detectors 16a, 16b (see FIG. 3) arranged facing the respective X-ray sources is determined. This imaging method, also known as dual-energy imaging, is used in the method shown in FIG. 1 for generating first and second measured projection data sets PMD1, PMD2, which are assigned to the respective different X-ray energy spectra $R_{E1}$, $R_{E2}$.

In step 1.V, the measured X-ray projection data PMD1, PMD2 that has been acquired is reconstructed into pseudo-monoenergetic image data BD ($E_3$), the virtual X-ray energy source assigned whereto has a low energy value $E_3$ compared with the mean energies $E_1$, $E_2$ of the first and second X-ray energy spectra. This energy value $E_3$ may be in the range from 40 to 45 keV for example, which corresponds to a virtual X-ray tube voltage of around 80 kV.

Subsequently, in step 1.VI, a filtering method is applied to the monoenergetic image data BD ($E_3$) that has been acquired, with which method the image noise in the pseudo-monoenergetic image data BD (E3) that has been acquired is reduced. Such a method is described for example in DE 10 2011 083 727 A1, the content of which is cited herewith in the present patent application. The filtered monoenergetic image data FBD ($E_3$) thus obtained at low energies $E_3$ has a higher contrast-noise ratio in conventional dual-source CT devices such as SOMATOM Definition Flash than images that have been acquired directly using mono-energy imaging techniques at low tube voltages. Compared with mono-energy images, the contrast-noise ratio increases by 20-50% here at the optimum tube voltage, as a function of the phantom size, which can be directly translated into a corresponding reduction in the radiation dose.

In step 1.VII there ensues the output of the filtered image data FBD ($E_3$), to a database or on an output screen, for example.

In the CT imaging method described in connection with FIG. 1, there ensues a combination of the advantages of the low image noise that occurs at high X-ray energies with the advantages of a high image contrast that occurs at low energies in the region of the energy of an absorption edge of a contrast agent that is used. Consequently, compared with a conventional procedure, in which image data is acquired using X-ray radiation with energies in the region of the energy value of an absorption edge of a contrast agent KM that is used, a much improved image contrast/noise ratio can be achieved, which leads to a considerably improved image quality of the CT imaging method or alternatively or additionally with a lower applied dose of X-ray radiation.

Figure 2:
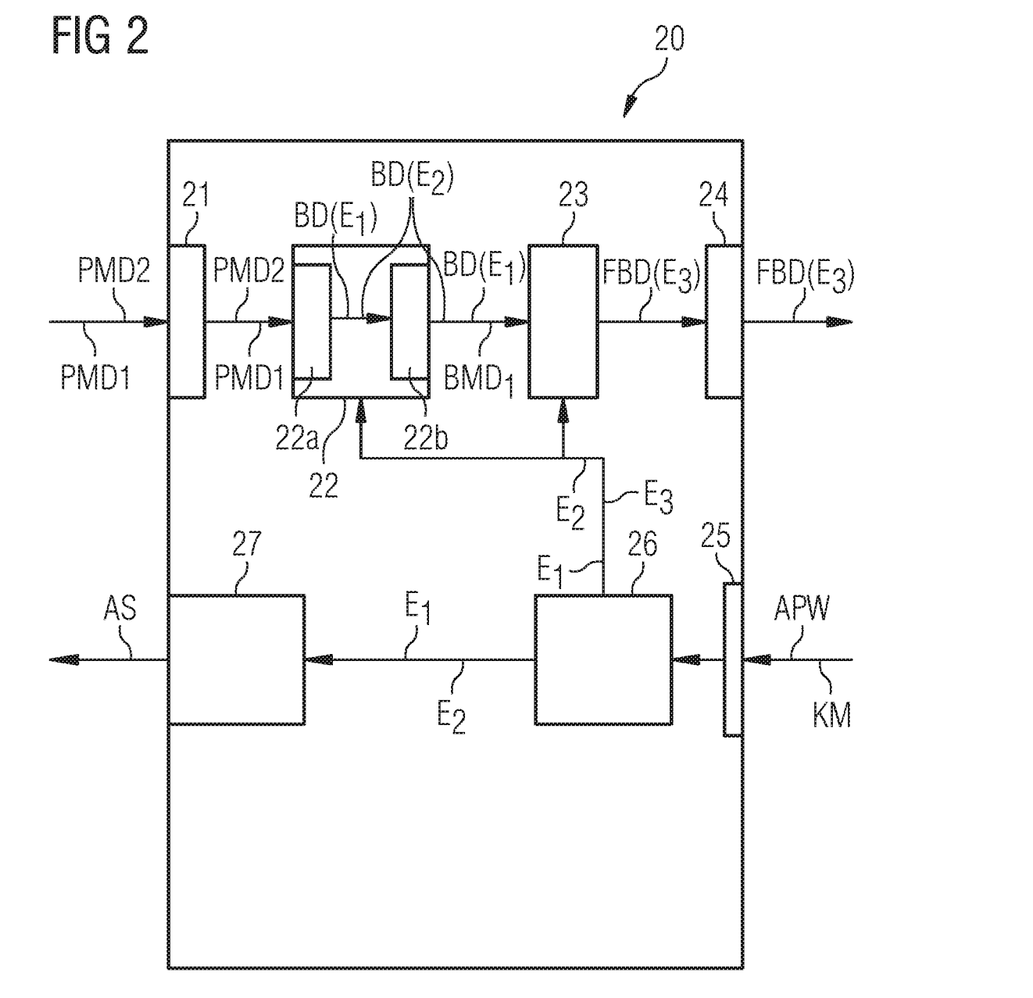
FIG. 2 shows a block diagram, with which an image data generating system according to one example embodiment of the invention is illustrated.

FIG. 2 shows in schematic form an image data generating device 20 according to one example embodiment of the invention. The image data generating device 20 comprises an input interface 25, with which data that provides information on the absorption properties of a region to be examined FOV of a patient who is to be examined, in particular dimension parameter values APW, together with data relating to the type of contrast agent KM administered to the patient before the start of the imaging method is acquired. The APW and KM data acquired by the input interface 25 is transmitted to an X-ray energy-determination unit 26. The X-ray energy-determination unit 26 determines values for a first mean energy $E_1$ of a first X-ray energy spectrum $R_{E1}$ and for a second mean energy $E_2$ of a second X-ray energy spectrum $R_{E2}$ as a function of a dimension parameter value APW relating to the subject to be examined or to the patient's X-ray radiation absorption that has been determined. Furthermore, the X-ray energy-determination unit 26 also determines a third X-ray energy value $E_3$, at which what are known as pseudo-monoenergetic image data BD ($E_3$) is acquired with the aid of the image data generating device 20. The mean energy values $E_1$, $E_2$, together with the energy value $E_3$, can be selected for example, such that a reduced radiation dose required for a desired image contrast/noise ratio is achieved in the imaging. The values acquired for the first and second mean energies $E_1$, $E_2$ are forwarded to a control unit 27 that generates activation signals AS based on the energy values $E_1$, $E_2$ that are received. The activation signals are forwarded to a control interface 34 (see FIG. 3) in the respective CT system. Furthermore, the values determined for the first and second mean energies $E_1$, $E_2$ and also for the third energy $E_3$ are forwarded to a reconstruction unit 22 that still remains to be explained and to a filtering unit 23 that still remains to be explained.

The image data generating device 20 shown in FIG. 2 additionally includes a measured projection data acquisition unit 21. The measured projection data acquisition unit 21 is used to acquire contrast-agent enhanced measured X-ray projection data PMD1, PMD2 using different energy spectra $E_1$, $E_2$ from an examination region FOV in an examination object O during the actual imaging process or also from a database in which the measured X-ray projection data PMD1, PMD2 has been stored. The measured X-ray projection data PMD1, PMD2 is generated in the imaging process by the examination region FOV being impacted by X-ray radiation with first and second X-ray energy spectra $R_{E1}$, $R_{E2}$ and the transmitted X-ray radiation being acquired by detectors that are separate from one another (see detectors 16a, 16b in FIG. 3). The measured X-ray projection data PMD1, PMD2 generated by the detectors and acquired by the measured projection data acquisition unit 21 is subsequently forwarded to an image data reconstruction unit 22, which reconstructs pseudo-monoenergetic image data BD ($E_3$) therefrom. The image data reconstruction unit 22 includes an individual image data reconstruction unit 22a. With the aid of the individual image data reconstruction unit 22a, individual images BD ($E_1$), BD ($E_2$) are first reconstructed for the first X-ray energy spectrum $R_{E1}$ and the second X-ray energy spectrum $R_{E1}$ or the respective first measured X-ray projection data PMD1 and the second measured X-ray projection data PMD2. These individual images BD ($E_1$), BD ($E_2$) are subsequently forwarded to an image-mixing unit 22b, which generates a first pseudo-monoenergetic mixed image $BDM_1$=BD ($E_3$) based on the individual images BD ($E_1$), BD ($E_2$) according to the following formula:

$$BD(E_3)=w(E_3) \cdot BD(E_1)+(1-w(E_3)) \cdot BD(E_2). \quad (1)$$

Here the composition w ($E_3$) is a function of a virtual energy $E_3$. The pseudo-monoenergetic image data $BDM_1$=BD ($E_3$) is assigned to this third virtual X-ray energy $E_3$.

Subsequently, the mixed pseudo-monoenergetic image data $BDM_1$ that has been generated is forwarded to a filtering unit 23, which reduces the image noise in the image data $BDM_1$ that has been generated. The filtering is achieved by at least one further mixed image $BDM_2$ or, in general (m−1), additional mixed images $BDM_2$ . . . $BDM_m$ being generated based on the individual images BD ($E_1$), BD ($E_2$) with coefficients $c_1$, $c_2$, which differ from the two coefficients w($E_3$) and (1−w($E_3$)) and also from one another in at least one coefficient. Subsequently, there ensues a generation of filtered image data FBD ($E_3$) according to:

$$FBD(E_3) = FBDM_1 = \sum_{j<=m} g_j(r)F_j BDM_j. \quad (2)$$

Yet, $FBDM_1$ is the filtered first mixed image $BDM_1$. The scaling function $g_1(r)$ has the value 1 and the other scaling functions $g_j(r)$ are defined, such that in the location r an image or an intensity value which corresponds to that of the first mixed image $BDM_1$, apart from noise.

The filters $F_j$ are spectral filters and are defined as follows:

$$\sum_{j<=m} F_j = 1, \quad (3)$$

wherein the individual spectral filters $F_j$ each break down the mixed images into frequency bands or energy components and the first spectral filter $F_1$ corresponds to a low pass filter which contains the frequency f=0 or the respective energy E=0 in full intensity.

As already mentioned, such a filtering method is described in DE 10 2011 083 727 A1, the entire contents of which are hereby incorporated herein by reference. The applications filed at the German Patent and Trademark Office with the application numbers 10 2015 223 601.4 and 10 2015 223 606.4, the entire contents of each of which are hereby incorporated herein by reference, describe filtering methods for reducing noise in X-ray images.

The filtered image data FBD ($E_3$) that has been made mainly noise-free is subsequently forwarded to an output interface 24, from which the filtered image data FBD ($E_3$) for example, is forwarded to a data storage unit (see FIG. 3, data storage unit 32) or to an display unit, on which it is displayed in image form.

Figure 3:
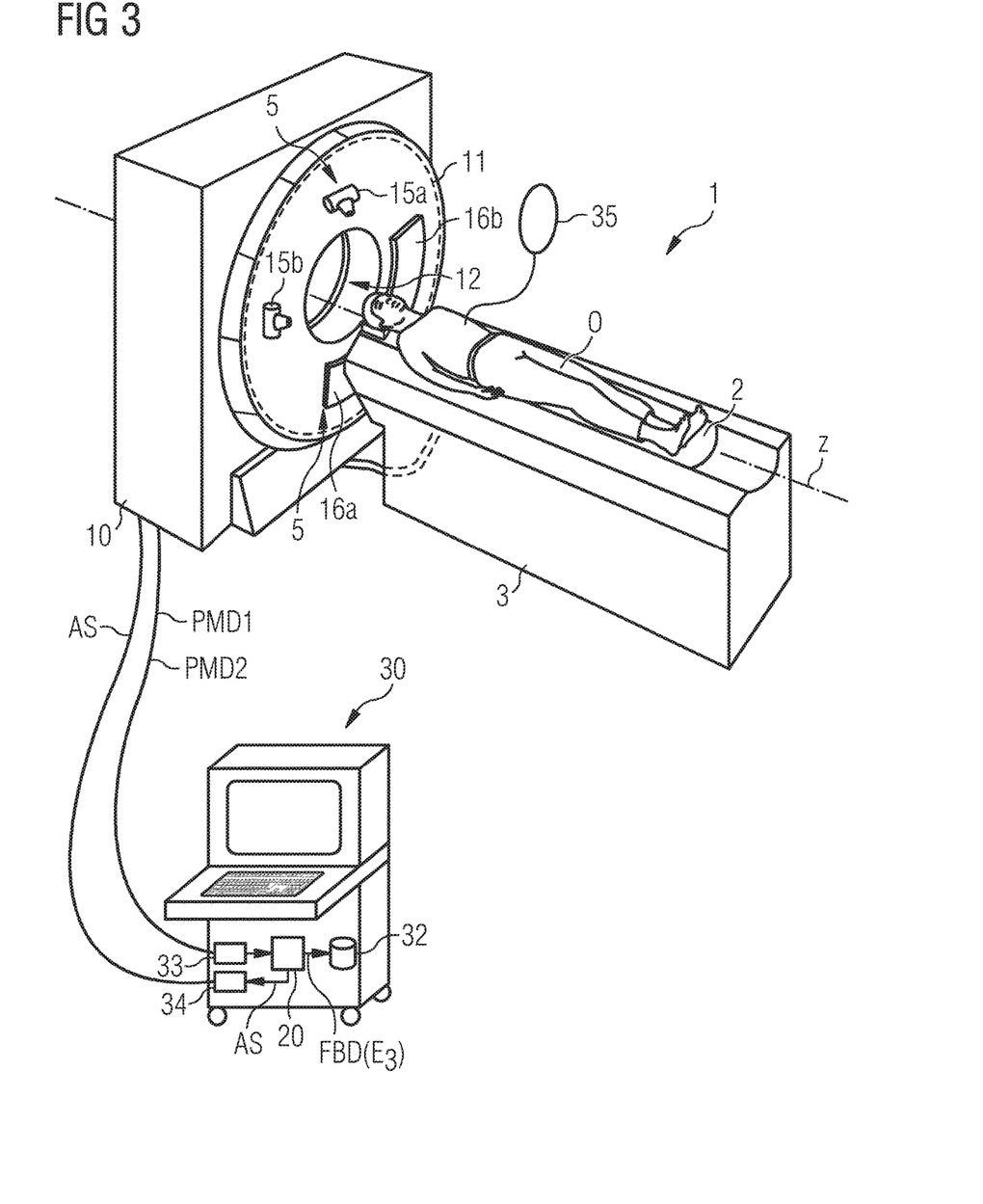
FIG. 3 shows a diagrammatic view of a computer tomography system according to one example embodiment of the invention.

FIG. 3 shows a computer tomography system 1 that includes the image data generating device 20, which was illustrated in FIG. 2. The CT system 1, which is designed as a dual-energy CT system essentially includes a conventional scanner 10, in which on a gantry 11, a measured projection data acquisition unit 5 with two detectors 16a, 16b and two X-ray sources 15a, 15b facing the detectors 16a, 16b circulates around a measurement space 12. In front of the scanner 10, there is a patient-positioning device 3 or a patient table 3, whose upper portion 2 can be moved to the scanner 10 with a patient O located thereon, in order to move the patient O through the measurement space 12 with respect to the detector system 16a, 16b. The scanner 10 and the patient table 3 are activated by a control device 30, from which come acquisition control signals AS via a conventional control interface 34, in order to activate the entire system according to given measurement protocols in the conventional manner. In the event of a spiral acquisition, a helix-shaped pathway ensues as a result of a movement of the patient O along the z-direction, which corresponds to the system axis z longitudinally through the measurement space 12, and the simultaneous circuit of the X-ray sources 15a, 15b for the X-ray sources 15a, 15b with respect to the patient O during the measurement. In this case, the detectors 16a, 16b always run in parallel to the X-ray sources 15a, 15b, in order to acquire measured projection data PMD1, PMD2, which is then used for reconstructing volume and/or slice image data. Likewise, a sequential measurement method can also be carried out, in which a fixed position in the z-direction is initiated and then during a circuit, a partial circuit or a plurality of circuits the required measured projection data PMD1, PMD2 is then acquired at the respective z-position, in order to reconstruct a cross-section image in this z-position or to reconstruct image data from the measured projection data for a plurality of z-positions. The method according to the invention can basically also be used on other CT-systems, for example, with only one X-ray source or a detector that forms a complete ring. For example, the method according to the invention can also be applied to a system with a patient table that has not moved and to a gantry that moves in the z-direction (what is known as a sliding gantry).

The measured projection data PMD1, PMD2 (also referred to hereinafter as raw data) acquired by the detectors 16a, 16b via a raw data interface 33 is forwarded to the control device 30. This raw data is then further processed, optionally after a suitable pre-processing in an image data generating device 20, which in this example embodiment is implemented in the control device 30 in the form of software on a processor. On the basis of the raw data PMD1, PMD2, this image data generating device 20 reconstructs pseudo-monoenergetic image data FBD ($E_3$) with the aid of the method according to an embodiment of the invention. The precise design of such an image data generating device 20 is shown in detail in FIG. 2.

The pseudo-monoenergetic image data FBD ($E_3$) generated by the image data generating device 20 is then stored in a memory 32 of the control device 30 and/or output in the usual manner on the screen of the control device 30. It can also be fed via an interface that is not shown in FIG. 3 into a network that is linked to the computer tomography system 1, for example, a radiological information system (RIS), and deposited in a mass memory that is accessible there or output as images on printers or filming stations that are connected thereto. The data can therefore be further processed in any manner and then stored or outputted. Via the image data generating device 20 there also ensues an acquisition of appropriate activation parameters or activation signals AS on the basis of data that has been input in advance, in particular of dimension parameter values APW. The activation signals are subsequently transmitted to the aforementioned control interface 34. From there, the units directly involved in the imaging, such as, for example, the X-ray sources 15a, 15b, the detectors 16a, 16b, and the patient couch 3 and so on, are then activated.

In addition FIG. 3 also shows a contrast-agent injection device 35, with which a contrast agent is injected into the patient O beforehand, that is, before the start of the CT imaging method 100. The dynamic properties of the contrast agent in a region that is to be examined can then be imaged with the aid of the computer tomography system 1 using the X-ray imaging method according to an embodiment of the invention 100.

The components of the image data generating device 20 can mainly or entirely be implemented in the form of software elements on a suitable processor. In particular, the interfaces between these components can also be designed in software form only. It is only desirable that opportunities exist for access to appropriate storage regions, in which the data can be appropriately stored temporarily and can be accessed again at any time and updated.

Finally, it is once again pointed out that the methods and installations described in the aforementioned are merely preferred example embodiments of the invention and that the invention can be varied by a person skilled in the art without going beyond the scope of the invention insofar as it is set out in the claims. Thus the method and the image data generating device have primarily been explained by way of a system for acquiring medical image data. However, embodiments of the invention is not restricted to an application in the medical field but basically the invention can also be applied to the acquisition of images for other purposes. For the sake of completeness, it is also pointed out that the use of the indefinite article "a" or "an" does not preclude the relevant features from being present in plurality. Likewise the term "unit" does not preclude this from consisting of a plurality of components that can optionally also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray imaging method for generating contrast-enhanced image data of an examination region of an object to be examined, comprising:
    acquiring first contrast-agent influenced measured X-ray projection data using a first X-ray energy spectrum and at least second contrast-agent influenced measured X-ray projection data using a second X-ray energy spectrum from the examination region; and
    reconstructing pseudo-monoenergetic image data to generate the contrast-enhanced image data of the examination region of the object, the pseudo-monoenergetic image data assigned to a third X-ray energy spectrum with a third mean energy, the third X-ray energy spectrum based on the acquired first and at least second measured X-ray projection data, wherein
    a mean X-ray energy of the first X-ray energy spectrum and a mean X-ray energy of the at least second X-ray energy spectrum are selected as a function of a dimension parameter value of the object to be examined.

2. The X-ray imaging method of claim 1, wherein,
    the mean energy of the first X-ray energy spectrum and the mean energy of the second X-ray energy spectrum correspond to a first image noise, and the mean energy of the third X-ray energy spectrum corresponds to a second image noise, the first image noise being less than the second image noise,
    the mean energy of the first X-ray energy spectrum and the mean energy of the second X-ray energy spectrum are both higher than the mean energy of the third X-ray energy spectrum, or
    the mean energy of the first X-ray energy spectrum and the mean energy of the second X-ray energy spectrum correspond to a first image noise, the mean energy of the third X-ray energy spectrum corresponds to a second image noise, the first image noise being less than the second image noise, and the mean energy of the first X-ray energy spectrum and the mean energy of the second X-ray energy spectrum are both higher than the mean energy of the third X-ray energy spectrum.

3. The X-ray imaging method of claim 1, wherein the X-ray imaging method includes a dynamic time-resolved imaging method.

4. The X-ray imaging method of claim 1, wherein an X-ray energy distribution around the mean X-ray energy of the third X-ray energy is used as a third X-ray energy spectrum, and wherein at the mean X-ray energy of the third X-ray energy, there is an increased contrast/noise ratio in the image data to be generated.

5. The X-ray imaging method of claim 1, wherein the third X-ray energy spectrum includes a distribution around a mean X-ray energy, the mean X-ray energy being near to an X-ray absorption edge of the contrast agent that is used for contrast enhancement.

6. The X-ray imaging method of claim 1, wherein the contrast agent includes iodine, and the third X-ray energy spectrum has a mean energy between 35 keV and 60 keV.

7. The X-ray imaging method of claim 1, wherein the dimension parameter value includes information relating to one of
    a body mass of the object to be examined,
    the dimensions of the the object to be examined,
    a body-mass index (BMI) of the object to be examined,
    a sub-combination thereof, or a combination thereof.

8. The X-ray imaging method of claim 1, wherein
    the acquiring includes using a multi-source CT system,
    wherein the first X-ray projection data is acquired simultaneously with the at least second measured X-ray projection data.

9. The X-ray imaging method of claim 1, wherein
    the acquiring includes using a single-source CT system with a single X-ray tube, and wherein the X-ray tube performs a rapid switchover of an electric voltage to acquire the first and at least second measured X-ray projection data.

10. The X-ray imaging method of claim 1, wherein the acquiring includes using a photon-counting X-ray detector.

11. The X-ray imaging method of claim 1, wherein the acquiring further includes:
    acquiring additional image data at a fourth X-ray energy with a high mean energy, based on the first and at least second measured X-ray projection data, and wherein,
    the additional image data corresponds to image data that is not contrast-enhanced,
    the reconstructing pseudo-monoenergetic image data includes using a filtering method to reduce image noise, or
    both the additional image data corresponds to image data that is not contrast-enhanced and the reconstructing pseudo-monoenergetic image data includes using a filtering method to reduce image noise.

12. An image data reconstruction device, comprising:
    an X-ray energy-determination unit configured to determine a mean energy of a first X-ray energy spectrum and a mean energy of at least a second X-ray energy spectrum as a function of a dimension parameter value relating to an object to be examined;
    a control unit configured to activate one or more of a plurality of X-ray sources in a CT system such that the one or more of the plurality of X-ray sources generates X-ray radiation respectively using each of the first X-ray energy spectrum and the at least second X-ray energy spectrum with the respectively determined first and at least second mean energy values;
    a measured projection data acquisition unit configured to acquire a first contrast-agent influenced measured X-ray projection data using the first X-ray energy spectrum and an at least second contrast-agent influenced measured X-ray projection data using the at least second X-ray energy spectrum, relating to an examination region in the examination object; and
    an image data reconstruction unit to reconstruct pseudo-monoenergetic image data, assigned to a third X-ray energy spectrum, based on the acquired first and at least second measured X-ray projection data.

13. A computer tomography system, comprising the image data generating device of claim 12.

14. A non-transitory computer program product, including a computer program, directly loadable into a memory unit of an image data generating device, including program segments to carry out the method of claim 1 when the computer program is run in the image data generating device.

15. A non-transitory computer-readable medium, including transferable and executable program segments of a computer program, stored by a processor unit of an image data generating device, to carry out the method of claim 1 when the program segments are run by the processor unit of the image data generating device.

16. The X-ray imaging method of claim 1, wherein the X-ray imaging method includes a CT X-ray imaging method.

17. The X-ray imaging method of claim 3, wherein the dynamic time-resolved imaging method includes a CT angiography method or a CT perfusion imaging method.

18. The X-ray imaging method of claim 2, wherein the X-ray imaging method includes a dynamic time-resolved imaging method.

19. The X-ray imaging method of claim 18, wherein the dynamic time-resolved imaging method includes a CT angiography method or a CT perfusion imaging method.

20. The X-ray imaging method of claim 2, wherein the third X-ray energy spectrum includes an X-ray energy distribution around a third mean X-ray energy, and wherein at the third mean X-ray energy, a contrast/noise ratio in the image data to be generated is greater than a contrast/noise ratio in the image data.

21. The X-ray imaging method of claim 6, wherein the third X-ray energy spectrum has a mean energy between 40 keV and 45 keV.

* * * * *

UNITED STATES PATENT AND TRADEMARK OFFICE
CERTIFICATE OF CORRECTION

PATENT NO.        : 10,420,522 B2                                  Page 1 of 1
APPLICATION NO.   : 15/428729
DATED             : September 24, 2019
INVENTOR(S)       : Thomas Flohr et al.

It is certified that error appears in the above-identified patent and that said Letters Patent is hereby corrected as shown below:

In the Claims

At Column 23, Line number 56, Claim 5 reads as 'contrast agent', but should read --contrast-agent--.

At Column 23, Line number 59, Claim 6 reads as 'contrast agent', but should read --contrast-agent--.

At Column 24, Line number 53, Claim 13 reads as 'data generating device', but should read --data reconstruction device--.

Signed and Sealed this
Nineteenth Day of November, 2019

Andrei Iancu
*Director of the United States Patent and Trademark Office*